United States Patent [19]

Olesen et al.

[11] Patent Number: Plant 6,265

[45] Date of Patent: Aug. 30, 1988

[54] ROSE PLANT NAMED POULANDER

[76] Inventors: Pernille Olesen; Mogens N. Olesen, both of Hillerodvej 49, DK 3480 Fredensborg, Denmark

[21] Appl. No.: 907,377

[22] Filed: Sep. 15, 1986

[51] Int. Cl.[4] ..... A01H 5/00

[52] U.S. Cl. ..... Plt./28

[58] Field of Search ..... Plt./28

*Primary Examiner*—Robert E. Bagwill
*Attorney, Agent, or Firm*—Vincent G. Gioia

[57] ABSTRACT

A new floribunda rose variety with flowers of currant red coloring.

1 Drawing Sheet

The present invention relates to a new and distinct variety of rose plant of the floribunda rose class, which was originated by my crossing as seed parent the rose known as "Royal Occasion" (U.S. Plant Pat. No. 3,824) and as pollen parent an unnamed, unpatented seedling of my creation. The denomination of the new rose is "Poulander".

Among the novel characteristics possessed by this new variety which distinguish it from its parents and all other varieties of which I am aware are flowers of warm currant red coloring borne in large sprays and of substantially unfading character. The flowers are attractively displayed against dense, dark green foliage. The flower's coloring is highlighted by good floribunda inflorescence form borne on a plant of unusually good disease resistance. Asexual reproduction by budding of the new variety as performed in Fredensborg, Denmark, shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Colour Chart (R.H.S.C.C.). The terminology used in color description herein refers to plate numbers in the aforementioned color chart, e./g., "46A" is plate 46A of the Royal Horticultural Society Colour Chart.

Parentage: Seedling.
*Seed parent.*—"Royal Occasion".
*Pollen patent.*—Unnamed seedling.
Class: Floribunda.

The following observations are made of specimens grown outdoors in Fredensborg, Denmark, during the month of October.

FLOWER

Blooming habit: Continuous.

A. Bud:
(1) *Size.*—Medium.
(2) *Form.*—Ovoid.
(3) *Color.*—When sepals first divide — near currant red, 46A.

(4) *Sepals.*—Long, fancy, often with some bract-like appendages.
(5) *Peduncle.*—Length — long. Aspect — straight. Strength — strong, erect. Color — near reddish green.

B. Bloom:
(1) Size.—Average size when fully expanded — about 6 to 8 mm.
(2) *Borne.*—Several together in large sprays.
(3) *Form.*—High centered at first, becoming flat when opened and somewhat ruffled at maturity.
(4) *Petalage.*—Number of petals under normal conditions — about 20.
(5) *Color.*—As sepals fall, the flower coloring becomes near 46B to C and stabilizes in this range to maturity. Occasional white streaking may be seen but color holds very well. Color at point of petal attachment is near white.

C. Petals:
(1) *Texture.*—Thick.
(2) *Appearance.*—Velvety inside and outside satiny.
(3) *Form.*—Broad fan shaped.
(4) *Arrangement.*—Regular, shingle-like.
(5) *Petaloids in center.*—Few.
(6) *Persistence.*—Drop off cleanly.
(7) *Fragrance.*—Slight.
(8) *Lasting quality.*—Long lasting on plant and as cut flower.

REPRODUCTIVE ORGANS

A. Stamens, filaments and anthers:
(1) *Arrangement.*—Regularly arranged around styles.
(2) *Color.*—Filaments — orange; anthers — yellow.

B. Pollen:
*Color.*—Pale yellow.

C. Styles: Medium, tightly bunched, even length.

D. Stigmas:
*Color.*—Yellow.

E. Hips:
*Shape.*—Globular.
*Size.*—1 to 2 cm.
*Color.*—Dark green, slightly orange when mature.
*Do seeds protrude?*—No.

PLANT

A. Form: Compact, spreading, bushy.

B. Growth: Very vigorous, branches well, tall.
*Height attained.*—About 80 to 120 cm.

C. Foliage: Compound 5 leaflets.

(1) *Size.*—Medium.
(2) *Quantity.*—Abundant.
(3) *Color.*—New and old foliage: Upper side — dark green. Under side — slightly lighter shade than upper side.
(4) *Shape.*—Oval.
(5) *Texture.*—Upper side is leathery, glossy and under side is dull.
(6) *Edge.*—Serrate.
(7) *Serration.*—Irregular.
(8) *Leaf stem.*—Color — dark green. Under side — dark green.
(9) *Stipules.*—Medium, pointed out, 15–20 mm.
(10) *Resistance to disease.*—Blackspot — good. Mildew — excellent. Rust — excellent.

D. Wood:
(1) *New wood.*—Color — green. Bark — smooth.

(2) *Old wood.*—Color — darker green. Bark — smooth.

E. Thorns:
(1) *Throns.*—Quantity (main stalk): numerous. On laterals from stalk — few. Form — straight. Length — medium. Color — reddish when young. Position — irregular.
(2) Prickles.—Profuse.

F. Winter hardiness: Winter hardy.

I claim:

1. A new and distinct variety of rose plant of the floribunda class, substantially as shown and described, characterized particularly by flowers of warm currant red coloring borne in large sprays and which maintain their color well through maturity.

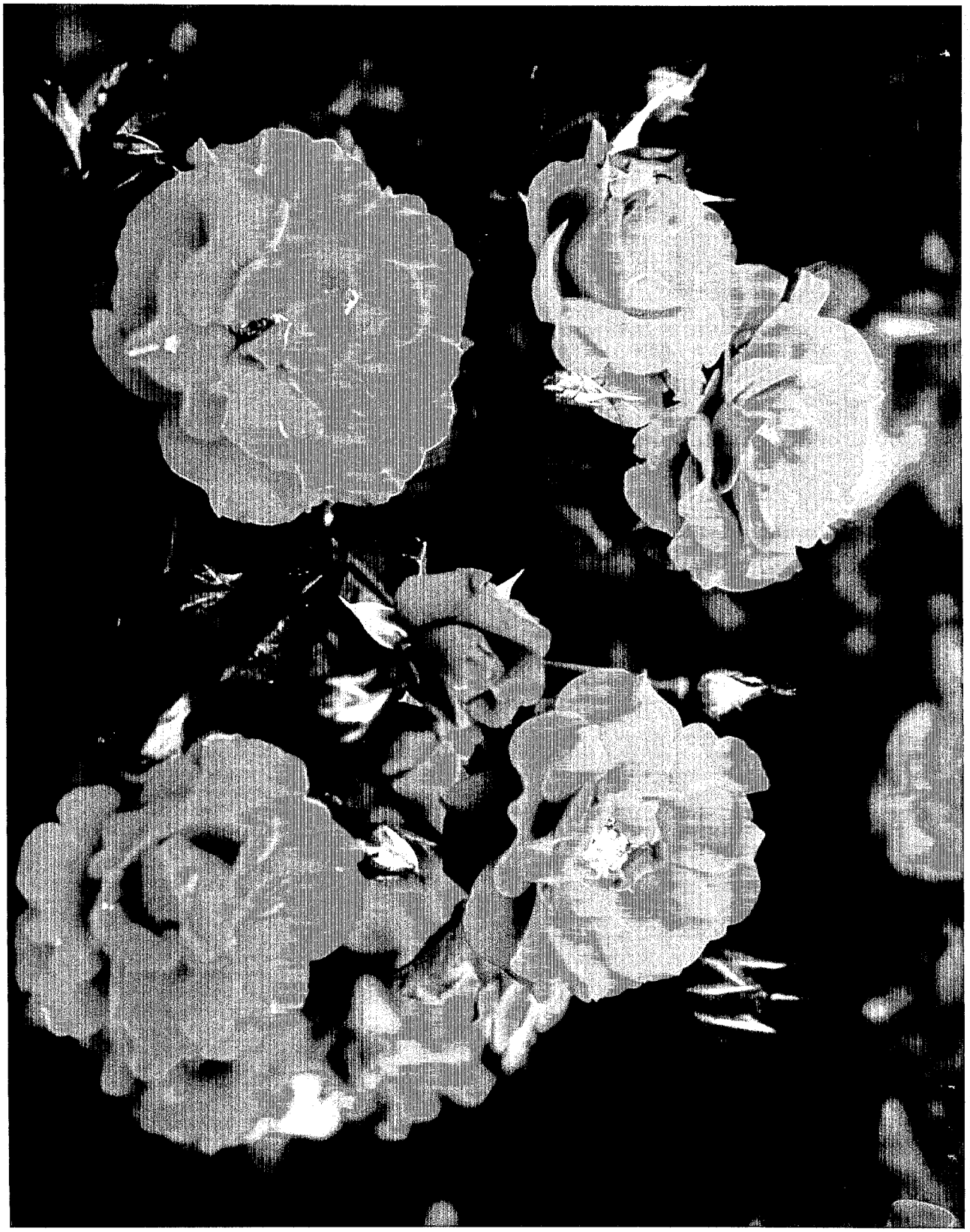

* * * * *